United States Patent [19]

Klose et al.

[11] Patent Number: 4,915,911
[45] Date of Patent: Apr. 10, 1990

[54] DEVICE FOR RINSING OUT A SUBSTANCE PRESENT IN A ZONE

[75] Inventors: Sigmar Klose, Berg; Manfred Pasch, Tutzing; Helmut Schlumberger, Polling; Wolfgang Kleeman, Tutzing; Friedhelm Vieth, Haunshofen, all of Fed. Rep. of Germany

[73] Assignee: Boehringer Mannheim GmbH, Mannheim, Fed. Rep. of Germany

[21] Appl. No.: 98,780

[22] Filed: Sep. 21, 1987

Related U.S. Application Data

[63] Continuation of Ser. No. 751,786, Jul. 3, 1985, abandoned.

[30] Foreign Application Priority Data

Jul. 6, 1984 [DE] Fed. Rep. of Germany ....... 3425009

[51] Int. Cl.$^4$ ............................................. G01N 21/07
[52] U.S. Cl. ......................................... 422/72; 356/246; 356/427; 422/102
[58] Field of Search ................ 422/64, 67, 72, 102, 422/61; 436/45; 356/244, 246, 426, 427; 494/26

[56] References Cited

U.S. PATENT DOCUMENTS 4,284,602 8/1981 Kelton .................................. 422/72
4,431,606 2/1984 Revillet ............................. 356/246
4,456,581 6/1984 Edelmann et al. .................. 356/246
4,515,889 5/1985 Klose et al. ............................ 422/64
4,557,600 12/1985 Klose et al. ............................ 436/45
4,558,555 5/1986 Provonchee ......................... 422/72

FOREIGN PATENT DOCUMENTS 73512 3/1983 European Pat. Off. ............. 422/72

Primary Examiner—Michael S. Marcus
Attorney, Agent, or Firm—Felfe & Lynch

[57] ABSTRACT

The present invention provides a device for rinsing out a substance present in a zone (d) with a liquid rinsing agent in several rinsing steps and for transferring the rinsing agent emerging from the zone (d) in the last rinsing step to a cuvette (K), wherein the zone (d) is present on a rotor (R) of variable speed of rotation, radially inwardly of the zone (d) on the rotor (R) there is provided a pump chamber (PK) for the rinsing agent which is connected with the zone (d) via a valve chamber (VK2) which fills, under the action of centrifugal force, above a predetermined speed of rotation, from the pump chamber (PK) and empties below the predetermined speed of rotation into the zone (d) and the zone (d) is connected with the cuvette (K) via a pipe (4) which, in one section, the axis of which has a component directed radially outwardly, is directed into a waste chamber (AK).

22 Claims, 3 Drawing Sheets

DEVICE FOR RINSING OUT A SUBSTANCE PRESENT IN A ZONE

This application is a continuation of application Ser. No. 751,786, filed July 3, 1985 now abandoned.

The present invention is concerned with a device for rinsing out a substance present in a zone with a liquid rinsing agent in several rinsing steps and for transferring the rinsing agent emerging from the zone in the last rinsing step to a cuvette.

It is an object of the present invention to modify a device for this type in such a manner that it does not require any moving inner parts for the liquid transport and is controllable in its manner of operation by the change of a single parameter.

Thus, according to the present invention, there is provided a device for rinsing out a substance present in a zone with a liquid rinsing agent in several rinsing steps and for transferring the rinsing agent emerging from the zone in the last rinsing step to a cuvette, wherein the zone is present on a rotor of variable speed of rotation, radially inwardly of the zone on the rotor there is provided a pump chamber for the rinsing agent which is connected with the zone via a valve chamber which fills, under the action of centrifugal force, above a predetermined speed of rotation, from the pump chamber and empties below the predetermined speed of rotation into the zone and the zone is connected with the cuvette via a pipe which, in one section, the axis of which has a component directed radially outwardly, is directed into a waste chamber.

As can be seen, the device does not have internal movable parts, the only parameter to be controlled being the speed of rotation of the rotor.

Valve chambers in the meaning of the present invention are described in U.S. patent application Ser. No. 413,011 (1980) issued as U.S. Pat. No. 4,557,600 on Dec. 10, 1985 and are there called "mixing valves". Therefore, a description of the construction and method of operation of these valve chambers is included by reference herein to U.S. Pat. No. 4,557,600 and the disclosures thereof are to be made a part of the disclosure of the present invention.

In order to be able to rinse the zone with precisely predetermined doses of the rinsing agent, according to a preferred feature of the present invention, between the pump chamber and the valve chamber, there is inserted a dosage chamber filling above a predetermined speed of rotation from the pump chamber with a predetermined volume of the rinsing agent and, below another predetermined speed of rotation, transfers this volume of the rinsing agent into the valve chamber.

In the case of another aspect of the present invention, for which independent patent protection is claimed there is provided a device for the portionwise transfer of a liquid from a pump chamber present on a rotor of variable speed of rotation into a run-off canal, characterized by a dosage chamber, following the pump chamber, with a small volume in comparison with the pump chamber, which has a preferably capillary run-off which, in the direction of the axis of rotation of the rotor, leads to a point which lies closer to the axis of rotation than the surface of the liquid in the pump chamber during rotation of the rotor with a first increased speed of rotation.

According to a preferred embodiment, the inlet and outlet of the run-off canal lie radially outside the pump chamber but the inlet lies radially closer to the pump chamber than the outlet.

In order that the flow of the rinsing agent on the path from the pump chamber into the dosage chamber is broken up into predetermined dosages, the dosage chamber is preferably connected with the pump chamber via a pipe constructed as a capillary breaking throttle, which pipe preferably has a widened inlet section. Furthermore, the above-mentioned outlet canal preferably leads into a chamber filled with an absorbent fleece which ensures a disturbance-free flow through the dosage chamber.

In order to be able to mix the rinsing agent with an additive, the pump chamber is preferably filled with a material which absorbs the rinsing agent, especially with a fleece. Furthermore, the pump chamber can be preceded by a substrate elution chamber which contains a fleece which absorbs the rinsing agent, which fleece can contain a substance with which the rinsing agent is to be mixed. Furthermore, the absorption material favours the break up of the flow in the above-mentioned capillary breaking throttle.

The function of the device is also influenced by its contact surface properties and surface characteristics. These contact surface properties can be influenced by the addition of surface-active agents, for example of detergents, to the liquid, to the fleece or to the device.

The surface characteristic can be altered, for example, by coating with hydrophobic or hydrophilic materials, by irradiation or by roughening.

BRIEF DESCRIPTION OF THE DRAWINGS

In the accompanying drawings are illustrated embodiments of the device according to the present invention.

The individual hollow spaces mentioned in the following description and their connections with one another are present between two assemblable synthetic resin parts.

The device according to the present invention serves for the rinsing of a substance present in a zone d with a liquid rinsing agent coming from a pump chamber PK in several rinsing steps and for transferring the rinsing agent emerging from the zone d in the last rinsing operation into a cuvette K. The zone d, the pump chamber PK and further zones which are described hereinafter, chambers and pipes are present between the two assembled synthetic resin parts on a rotor R, which can be rotated about an axis X—X with a variable speed or rotation. The pump chamber PK is present radially inwardly of the zone d between the two synthetic resin parts on the rotor R. The pump chamber PK is connected with the zone d via a valve chamber VK2 which, under the action of the centrifugal force, fills above a predetermined speed of rotation from the pump chamber PK and empties below the predetermined speed of rotation into the zone d. The zone d is connected with the cuvette K via a pipe 4 which, in a section 6, the axis of which has a component directed radially outwardly, is directed into a waste chamber AK.

Figure 3:
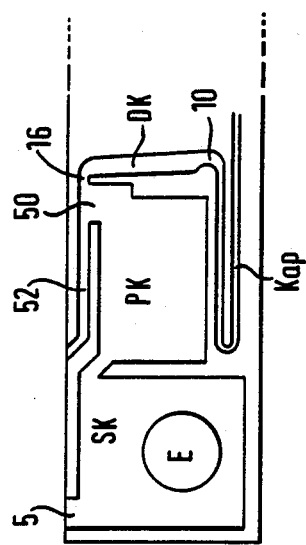
FIG. 3 illustrates an enlarged cross-sectional view of a substrate elution chamber upstream from the pump chamber of the insert device.

In the embodiment shown in FIG. 3 the pump chamber PK passes over, on its radially inner end, upwardly into an upwardly open substrate elution chamber SK. Between the pump chamber PK and the valve chamber VK2 is inserted a dosage chamber DK filling above a predetermined speed of rotation with a predetermined volume of the rinsing agent from the pump chamber PK and, below another predetermined speed of rotation, transfers this volume of rinsing agent into the valve chamber VK2. The dosage chamber DK has a run-off capillary Kap, the inlet 10 and outlet 12 of which lie radially outside the pump chamber PK but the inlet 10 of which lies closer to the pump chamber PK than its outlet 12.

The dosage chamber DK is connected with the pump chamber PK via a pipe 16 constructed as a capillary breaking throttle, the inlet of which is connected to a radially outer upper corner of the pump chamber PK.

Between a fleece in the pump chamber PK and the pipe 16, constructed as a capillary breaking throttle, there is present a chamber 50, preferably not filled with fleece, of greater cross-section than the pipe 16. This chamber 50 is preferably connected with an air-inletting tap line 52, which prevents a reduced pressure formation between the absorbing fleece in the pump chamber PK and the liquid in the dosage chamber DK in the breaking procedure.

Figure 1:
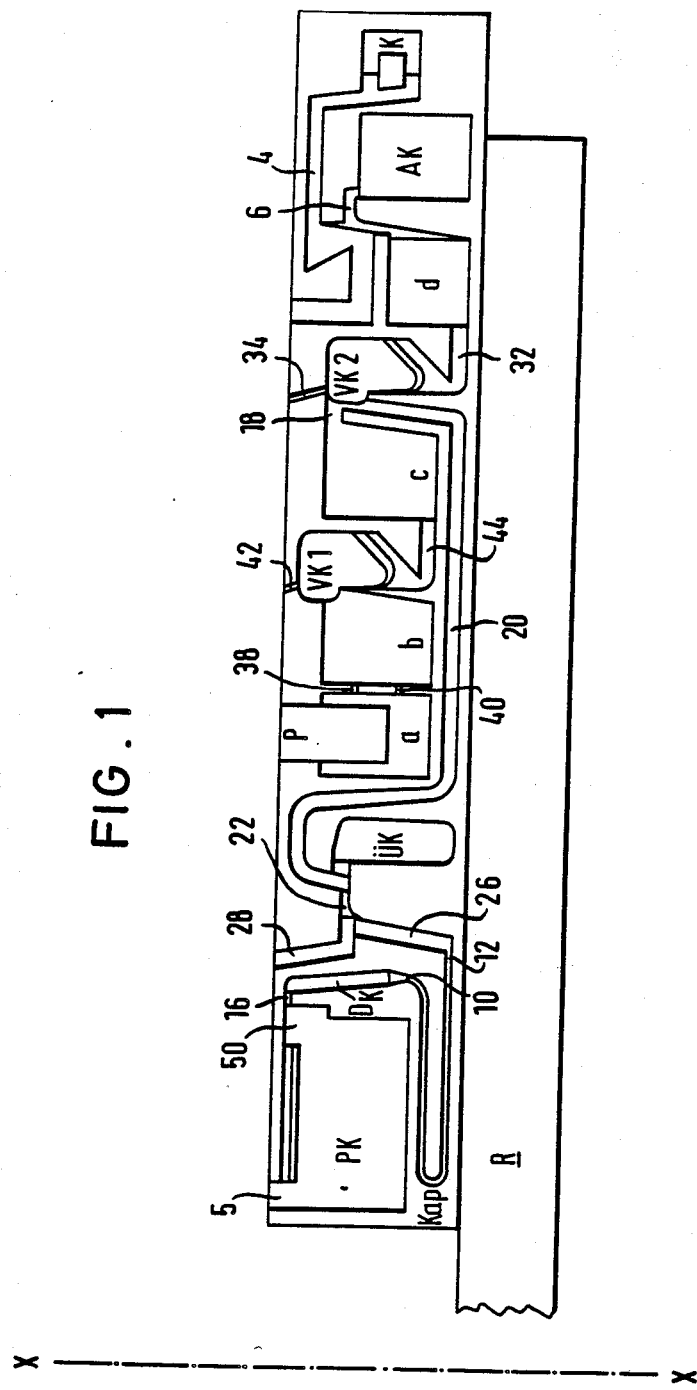
FIG. 1 is a cross-sectional view in side elevation of the rotor inset device.

According to FIG. 1, from the outlet 12 there leads a pipe 26 via a capillary 22 into an overflow chamber ÜK. The pipe 26 is vented in an upward direction by a pipe 28.

The overflow chamber ÜK is connected with the valve chamber VK2 by a pipe 20.

The valve chamber VK2 is connected with the zone d by a pipe 32. In an upward direction, the valve chamber VK2 is vented by a tap line 34. Radially inwardly of the valve chamber VK2, there lie (radially from inwards to the outside), a zone a with a sample application point P, a zone b, which is connected with the zone a by two short connecting pipes 38 and 40, a valve chamber VK1, which is connected with the zone b and, in upward direction, is vented by a tap line 42, as well as a zone c, which is connected via an inlet pipe 44 with the valve chamber VK1 and via an outlet pipe 18 with the valve chamber VK2.

For simple reactions or non-critical reagents, the zone b and/or VK1 and zone c can be omitted.

In the case of the preferred embodiment described hereinafter, the device is used for carrying out immunological determinations according to the Enzyme immunoassay (EIA) (EIA) principle with the use of a bound phase. The bound phase, which contains enzyme-marked antibody in a form bound via antigen to be determined and in free form, is washed out in several rinsing steps with a substrate solution for the marking enzyme which serves as wash liquid. This requires very short rinsing cycles and a careful separation of the wash liquid from the part of the substrate solution which, in the last rinsing step, serves as measurement liquid.

The pump chamber PK is filled with substrate solution or contains the substrate impregnated on fleece. The advantage of using substrate dried on fleece is the better stability of the dry reagent in comparison with solutions and the simpler storage of only one diluent for the sample and the substrate.

It is a disadvantage that, when the substrate (+buffer) is applied to the fleece of the pump chamber PK, in the case of application of the diluent, a concentration gradient forms which, because of the fleece present, cannot be broken down.

This disadvantage is overcome by the insertion of the substrate elution chamber SK. This chamber SK is, for example, 3.5 mm. deep and contains a substrate fleece of 1 mm. thickness on to which has been applied in concentrated form the necessary amounts of substrate and buffer in dry form. Furthermore, the chamber SK can contain an iron disc E coated, for example, with synthetic resin and of, for example, about 0.5 mm. thickness, which disc can be moved by externally arranged magnets. After application of diluent (application point (5)), there is achieved an elution of substrate and buffer from the fleece, as well as a complete homogenisation of the solution. In the case of the first centrifuging, the substrate solution is conveyed into the pump chamber PK and, in part, into the dosage chamber DK and thereafter behaves like a liquid pipetted substrate solution. The advantages of a homogeneous solution can thereby be combined with those of better stability and diluent storage.

The construction, use and method of operation of the device are, in this embodiment, as follows:

A diluted sample is introduced into a fleece in the zone a and a dilution agent is introduced into a substrate-containing fleece in the pump chamber PK and the rotor R is set in motion. The diluted sample dissolves from the buffer fleece in zone b the necessary amount of buffer, passes into the first valve chamber VK1, is conveyed from there, by reduction of the speed of rotation of the rotor R, into a conjugate fleece in the zone c, dissolves conjugate from this and passes into the second valve chamber VK2, where a reaction antigen+conjugate antibody-enzyme takes place. In the case of reduction of the speed of rotation of the rotor R, the solution is sucked out of the valve chamber VK2 into a separating fleece in the zone d and there comes into contact with bound antibody. The complexes of antigen-conjugate antibody-enzyme are here bound. Thereafter, the solution with the non-bound conjugate is centrifuged into the waste chamber AK. Parallel thereto, the dilution agent dissolves substrate out of the substrate-containing fleece in the pump chamber PK. The substrate solution formed, which serves as wash liquid, passes from there into the dosage chamber DK, where a precise dosing takes place, then partly into the overflow chamber ÜK or directly into the second valve chamber VK2 and then to the separation fleece in the zone d. By periodic acceleration and retarding of the rotor R, the wash liquid is centrifuged in the dosages which in the following description are also called "portions" ascertained by the dosing chamber DK from the separation fleece in the zone d into the waste chamber AK. If the waste chamber AK is filled, a portion of substrate solution is centrifuged into the cuvette K and there measured.

The speed of rotation programme of the rotor R is somewhat as follows: for the dosing of each "portion", the speed of rotation is increased to such an extent that the liquid is centrifuged out of the fleece present in the pump chamber PK against the capillary forces acting therein and is transported via the breaking throttle 16 into the dosage chamber DK. The run-off capillary Kap is thereby initially only partly filled because, in this state, the capillary force in the radially inwardly directed part of the run-off capillary Kap is smaller than the centrifugal force. Thereafter, the speed of rotation is reduced to such an extent that, in the radially inwardly directed part of the run-off capillary Kap, the capillary force preponderates over the centrifugal force. The run-off capillary Kap is thereby fully sucked out and, at the same time, the liquid connection between the dosage chamber DK and the pump chamber PK is broken in the region of the breaking throttle 16. The run-off capillary Kap fills completely up to its outlet 12, where the liquid remains stationary in the case of the mentioned reduced speed of rotation. Thus, in the dosage chamber DK and in the run-off capillary Kap, there is available a definite volume of liquid. This is emptied when the speed of rotation is again increased. Since, namely, the outlet 12 lies radially further outwardly than the inlet 10, the run-off capillary Kap acts like siphon in the field of the centrifugal force. In the case of this increase of the speed of rotation, care is to be taken that it is not so great that already fresh liquid passes out of the fleece in the pump chamber into the dosage chamber DK. On the contrary, this must first be the case when the dosage chamber DK is emptied and, for the introduction of a new dosage cycle, the speed of rotation is again increased as initially described.

In the case of the embodiment according to FIG. 1, at the end of the capillary there should be present a further hollow space not filled with fleece which prevents a spontaneous emptying of the capillary by capillary force. The capillary is then only emptied when, in the case of increasing the speed of rotation, the centrifugal force is greater than the capillary force. Furthermore, the hollow space at the end of the capillary prevents liquid from being sucked back from the following fleece in the overflow chamber against the general direction of transport.

Figure 2:
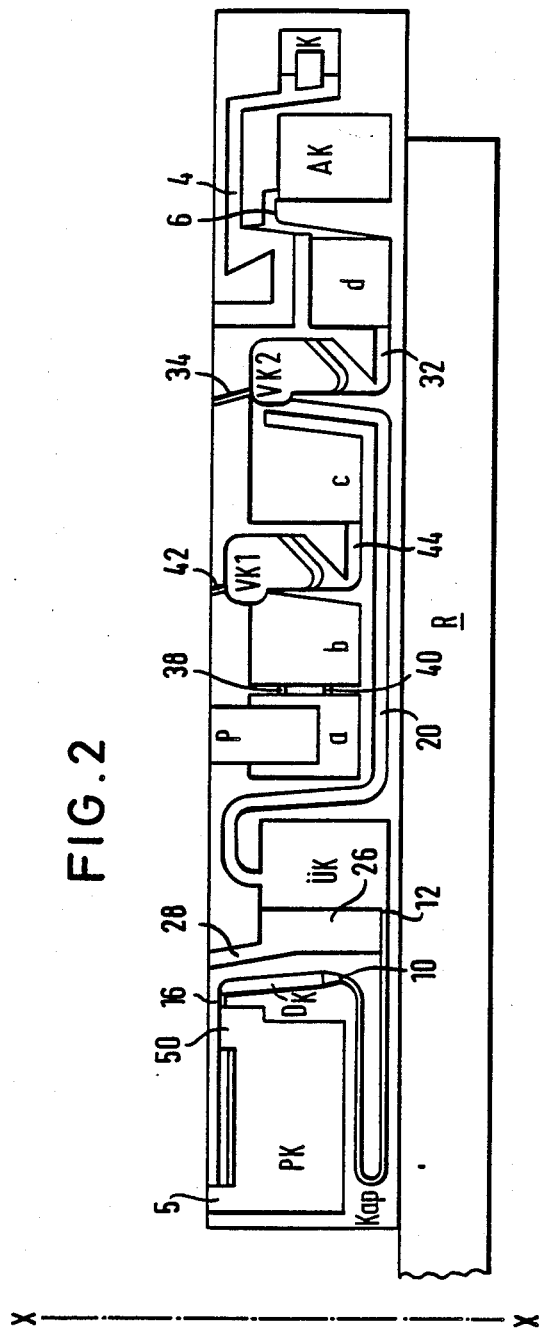
FIG. 2 illustrates a cross-sectional view in side elevation of a second embodiment of the rotor insert device.

In the case of the embodiment according to FIG. 2, an emptying of the dosage chamber DK and run-off capillary Kap can also take place when the rotor R is stationary since the radially inner side of the overflow chamber ÜK bounds on to the outlet 12 of the capillary Kap. A fleece in the overflow chamber ÜK sucks up the liquid coming from the dosage chamber DK as soon as the capillary Kap has filled. In the case of such an embodiment, it is not necessary that the outlet 12 of the capillary Kap lies radially further outwardly than its inlet. It is especially advantageous in this embodiment that, in the case of a low speed of rotation of the rotor R, the "portions" still running through are held back.

It is important that the liquid column in the dosage chamber DK, which, for example, holds exactly 29 μl. of liquid, breaks off cleanly in the direction of the pump chamber PK. The capillary breaking throttle 16 of the dosage chamber DK in the direction of the pump chamber PK must, therefore, have a quite definite diameter, which is dependent upon the surface properties of the substrate solution and of the wall material.

The overflow chamber ÜK preferably contains an absorbent medium, especially paper, in order to fix a definite volume. It is also possible to provide a conventional hollow space which is connected via a capillary 22 with the outlet 12 of the dosage chamber DK. The liquid drop forming in such a capillary 22 then prevents a runback of substrate solution from the overflow chamber ÜK into the outlet capillary Kap of the dosage chamber DK. However, a prevention of this runback by an absorbent medium in the overflow chamber UK proves to be better.

The section 6 of the pipe 4 between the zone d containing the separation fleece and the waste chamber AK must be such that no capillary forces are effective over its length. Only in this way is it possible to prevent fine droplets of the substrate solution, which are to pass into the waste chamber AK, by-passing the waste chamber AK and passing directly into the cuvette K. In order to achieve this, the surface of this section 6 is preferably provided with a covering of flakes of polytetrafluoroethylene. These flakes can be obtained with the use of a spray which contains the polytetrafluoroethylene in extremely finely divided form. On the inner surface of the section 6 there are thus formed tiny flakes of polytetrafluoroethylene which have a hydrophobing action and prevent at least a backflow of droplets. Under certain conditions, an increased surface roughness of the inner surface in this region can also be sufficient.

The device according to the present invention provides in a disposable on a centrifugal analyser the possibility, without the use of any mechanical parts, of successively producing several portions of liquid, the volume of which is precisely ascertained and is, especially, exactly reproducible. In the case of a disposable analytical element of the here-described kind, this is of especial importance because the total volume balance must be determined very exactly. The waste chamber before the cuvette is to be filled in such a manner that there is present in it, before the last rising step, an amount of liquid which fills the chamber very exactly within relatively narrow tolerances but does not overflow from the waste chamber. The tolerance of the filling of the waste chamber is thereby about 5%.

The pump chamber is to be made so large that its volume corresponds to a plurality of portions and, with the help of the breaking throttle, which cooperates with the fleece contained in the pump chamber, a separation of individual portions is possible.

In the case of a high speed of rotation, there is produced a uniform liquid level (regarded in the radial direction) in the pump chamber, in the dosage chamber and in the outlet capillary.

The outlet capillary extends radially inwardly to such an extent that it can thereby not run out completely, thus radially further inwardly than corresponds to the highest liquid level in the pump chamber. In the case of a reduction of the speed of rotation, the liquid breaks off precisely at a definite point between the dosage chamber and the pump chamber. Therefore, the volume of the dosage chamber up to the break-off point and the corresponding partial volume of the outlet capillary determine the size of the portion. In the region of the breaking throttle, the counteracting suction forces act, on the one hand, in the fleece of the pump chamber (there act counter to the general liquid transport direction) and, on the other hand, in the run-off capillary (these act in the general liquid transport direction). The force relationships are thereby such that the capillary forces in the fleece are considerably greater than in the run-off capillary. Consequently, in the case of reduction of the speed of rotation without the breaking throttle, the liquid would flow back quickly into the fleece. However, the flow resistance of the breaking throttle is so determined that, at the moment that the flowback commences, a breaking takes place at the appropriate point.

In order to fulfil this function, three measures are preferably to be met: The breaking throttle must have a sufficiently great flow resistance. This is ascertained by the properties of the liquid, for example the viscosity or contact surface properties, the surface characteristic and the cross-section of the breaking throttle. Especially preferred measures for the suitable change of the contact surface properties and/or of the flow properties in the region of the breaking throttle are described hereinbefore.

Positioned before the breaking throttle in the direction of the pump chamber, there is to be a chamber which is not filled with fleece, the cross-section of which is greater than that of the breaking throttle. An air introduction (52) should be present through which the hollow volume resulting in the case of the flowback of the liquid before the breaking throttle is filled; in other words, the space between the fleece and the breaking edge must be aerated.

Figure 4:
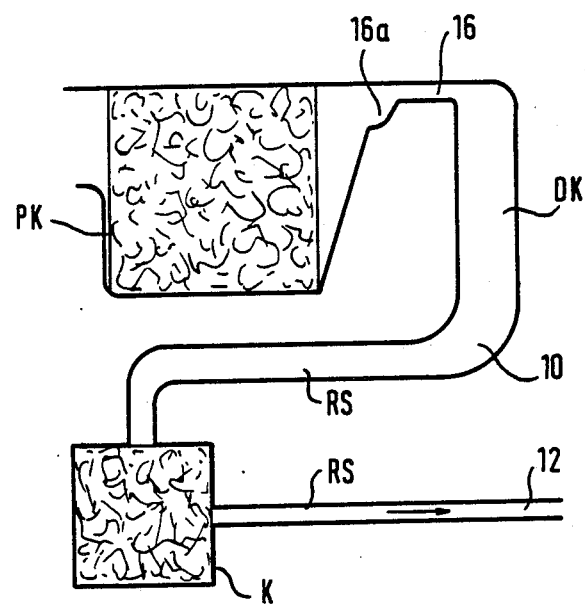
FIG. 4 illustrates a cross-sectional view in side elevation of a second embodiment of the connection between the pump chamber and dosage chamber.

In the case of the embodiment according to FIG. 4, the pump chamber PK is connected with the dosage chamber DK via a pipe 16, constructed as a capillary breaking throttle, which has a widened inlet section 16a. The pump chamber PK is made capillary-active and, for this purpose, preferably contains a fleece. In this case, the dosage chamber DK passes, without a recognisable transition in the region 10, into a run-off canal RS. The run-off canal RS leads in the direction of the axis of rotation X—X of the rotor R up to a point which lies closer to the axis of rotation X—X than the surface of the liquid in the pump chamber PK during the rotation of the rotor R with a first increased speed of rotation and then continues radially from the axis of rotation X—X. In the radially inner region, the run-off canal RS passes through a chamber K which contains an absorbent fleece.

In the case of the embodiment according to FIG. 4, the volume of the run-off canal RS is larger than in the previously described embodiment, in which the run-off canal RS is constructed as a capillary and is, therefore, designated with Kap. Since, as mentioned hereinbefore, the size of the portions is determined not only by the volume of the dosage chamber but also by the part volumes of the run-off canal filled during the first increased speed of rotation, the differences in the volume of the individual portions are the greater, the greater is the cross-section of the run-off canal. However, for many purposes of use, an especial uniformity of the dosages does not matter but only the fact that the total dosage of a plurality of dosages is, with sufficient exactitude, reproducibly the same. The embodiment according to FIG. 4 is especially suitable for such purposes.

It is important for the function that the outlet canal RS from the dosage chamber DK is conducted in such a manner that at least a part of it lies radially closer to the axis of rotation X—X of the rotor R than the surface of the liquid in the pump chamber PK during a rotation with a first increased speed of rotation. In the case of a non-capillary construction of the run-off canal RS, the liquid flows from the dosage chamber only due to gravitational force when the speed of rotation is reduced to a second, lower value. It is sucked up by the fleece in chamber K. Alternatively or additionally, the run-off canal can here also be constructed as in FIG. 1 in such a manner that its outlet lies radially outwardly of the dosage chamber.

I claim:

1. Apparatus for transfer of a liquid comprising a rotor which rotates about an axis of rotation, a first chamber disposed on said rotor and having a defined volume and an upper portion and a lower portion, a second chamber disposed on said rotor radially outward relative to said first chamber on said axis of rotation, a third chamber having an upper portion and a lower portion and a defined volume which is less than the volume of said first chamber, said third chamber positioned radially between said first and second chamber, wherein the upper portion of said first chamber is connected to the upper portion of said third chamber by a first pipe means characterized as a capillary breaking throttle means joining said first chamber to said third chamber from a point on the upper portion of said first chamber, said first pipe means being positioned at least partially radially outward on said axis of rotation, and said lower portion of said third chamber is connected to said second chamber by a second pipe means, said second pipe means having a first capillary section which leads from the lower portion of said third chamber, said second pipe means being positioned at least partially radially inward on said rotor and a second capillary section leading from the furthest radially inward point of said first capillary section, and said second capillary section having a component portion positioned radially outward with respect to said second chamber.

2. Apparatus of claim 1, wherein said first chamber further comprises means for admitting said liquid into said chamber.

3. Apparatus of claim 1 wherein said first pipe means has an inlet section connected to said first chamber which is wider than an inlet section connected to said third chamber.

4. Apparatus of claim 1, wherein said first chamber contains a liquid absorbing material.

5. Apparatus of claim 1, wherein said first chamber contains a wad of liquid receiving material and a pipe means connecting said first and second chambers, said pipe means extending from a radially outward region of said first chamber to a radially inward section of said second chamber, said pipe means ascending up from said first chamber, said pipe means having a top air escape means.

6. Apparatus of claim 1 further comprising a first valve chamber positioned on said rotor in a radially outward direction from said second chamber, said first valve chamber to said second chamber by means permitting transfer of a liquid sample from said second chamber to said first valve chamber.

7. Apparatus of claim 6, further comprising at least one reaction zone chamber extending in a radially outward direction from the axis of rotation and connected to said first valve chamber, said reaction zone chamber having an opening for admission therein of a second liquid agent.

8. Apparatus of claim 7 further comprising a second valve chamber extending radially outward from the axis rotation and connected by connecting means to both the reaction zone chamber and the first valve chamber.

9. Apparatus of claim 1, wherein said first chamber contains an empty portion having a greater cross sectional area than said first pipe means.

10. Apparatus of claim 9, wherein said empty portion of said first chamber is connected to an air-inlet tap line means.

11. Apparatus of claim 1, wherein said second chamber contains a liquid absorbing material.

12. Apparatus of claim 11, wherein said liquid absorbing material is fleece.

13. Apparatus of claim 11 wherein said liquid absorbing material is paper.

14. Apparatus of claim 1, wherein said second capillary section is connected to said second chamber via a third pipe means, said third pipe means being connected to a branched venting pipe means.

15. Apparatus of claim 14, wherein said third page means and said venting pipe means are connected at a point defining a capillary means.

16. Apparatus of claim 1, further comprising a fourth chamber radially inward of said first chamber on said rotor which is connected to said first chamber via a connecting means.

17. Apparatus of claim 16, wherein said fourth chamber contains a liquid absorbing material.

18. Apparatus of claim 16, wherein said fourth chamber contains a stirring means.

19. Apparatus of claim 18, wherein said stirring means is magnetically operated.

20. Apparatus for transfer of a liquid comprising a rotor which rotates about an axis of rotation, a first chamber disposed on said rotor and having a defined volume, a upper portion and a lower portion, a second chamber disposed on said rotor radially outward relative to said first chamber on said axis of rotation, a third chamber having an upper portion, a lower portion, and a defined volume which is less than the volume of said first chamber, wherein said third chamber is positioned between said first and second chamber, wherein the upper portion of said first chamber is connected to the upper portion of said third chamber by a first pipe means characterized as a capillary breaking throttle means joining said first chamber to said third chamber from a point on the upper portion of said first chamber, said first pipe means being positioned at least partially radially outward on said axis of rotation, said lower portion of said third chamber being connected to an upper portion of a fourth chamber containing an absorbent fleece by a second pipe means, and said forth chamber being connected to said second chamber by a third pipe means, wherein said second pipe means has a component which leads radially inward from said third chamber to said fourth chamber and said third pipe means has a component which leads radially outward from said fourth chamber.

21. Apparatus for transfer of a liquid comprising:
a rotor rotatable about an axis of rotation;
a first chamber positioned on said rotor containing a wad of liquid receiving material;
a second chamber positioned radially outward on said rotor with respect to said first chamber;
a third chamber positioned radially outward on said rotor with respect to said second chamber;
a first pipe means connecting said first and second chambers, said pipe means extending from a radially outward region of said first chamber to a radially inward section of said second chamber, said pipe means ascending upward from said first chamber and having a hydrophobic or rough inner surface; and
a second pipe means branching from said first pipe, said second pipe ascending up and connecting with said third chamber, said second pipe having a top air escape means.

22. Apparatus of claim 21, wherein said inner surface is coated with polytetrafluoroethylene.

* * * * *